United States Patent [19]
Earhart et al.

[11] Patent Number: 5,385,879
[45] Date of Patent: Jan. 31, 1995

[54] CARBONLESS PAPER SOLVENT COMPRISING DIISOPROPYLMETHYLNAPHTHALENE AND PRODUCTS UTILIZING SAME

[75] Inventors: Harold W. Earhart, Corpus Christi, Tex.; Andrew P. Komin; Dustin K. James, both of Wichita, Kans.

[73] Assignee: Koch Industries, Inc., Wichita, Kans.

[21] Appl. No.: 966,295

[22] Filed: Oct. 26, 1992

[51] Int. Cl.$^6$ .............................................. B41M 5/12
[52] U.S. Cl. ..................... 503/213; 106/311
[58] Field of Search .............. 503/213; 252/364; 106/311, 21 E

[56] References Cited

U.S. PATENT DOCUMENTS

| | | | |
|---|---|---|---|
| 3,806,463 | 4/1974 | Konishi et al. | 252/316 |
| 3,846,331 | 11/1974 | Konishi et al. | 252/364 |
| 4,003,589 | 1/1977 | Konishi et al. | 282/27.5 |
| 4,071,469 | 1/1978 | Vincent et al. | 252/364 |
| 4,236,732 | 12/1980 | Murakami et al. | 503/213 |
| 4,383,705 | 5/1983 | Okada et al. | 282/27.5 |

FOREIGN PATENT DOCUMENTS 7403521 10/1974 Netherlands ................. B41M 5/12

OTHER PUBLICATIONS

Ishizawa, N. et al., "Process Oils For Light-Resistant Rubber Compositions", Chem. Ab. 86(6): 30825r. of JP 51103951, Sep. 1976.

Takenori Kodama, Bulleitn of Aichi Environmental Research Center, No. 4, pp. 114–117 (1976) no month available.

Primary Examiner—Paul Lieberman
Assistant Examiner—Margaret Einsmann
Attorney, Agent, or Firm—Shook, Hardy & Bacon

[57] ABSTRACT

A carbonless paper solvent is provided comprising diisopropylmethylnaphthalene, generally in an amount of from 20% to 100% of the total weight of the solvent. The solvent is combined with a chromogenic substance and is encapsuled into microcapsules. The microcapsules are applied to a sheet of material and a color developing substance is then applied to another sheet to form a carbonless marking system. When the microcapsules are ruptured, the solubilized chromogenic substance contacts and reacts with the developer to form an image. In a method of the invention, a byproduct fraction consisting of components with a boiling point range of 200° to 400° C. are contacted with propylene under conditions sufficient to form an alkylation product comprising diisopropylmethylnaphthalene.

2 Claims, No Drawings

CARBONLESS PAPER SOLVENT COMPRISING DIISOPROPYLMETHYLNAPHTHALENE AND PRODUCTS UTILIZING SAME

BACKGROUND OF THE INVENTION

This invention relates in general to solvents for use in solubilizing dyes and, more particularly, to solvents used in the production of carbonless paper, microcapsules containing a chromogenic compound solubilized by such solvents, and pressure sensitive marking and recording material coated with such microcapsules. The invention also relates to a process for making carbonless paper solvents.

Carbonless paper and other marking systems depend upon localized contact between a chromogenic compound such as a leuco dye and a color developing substance to produce a visible indicia. In such marking systems, the dye is solubilized in a solvent and the dye and solvent are then emulsified in an aqueous solution to form tiny "oil" droplets. The oil droplets are then encapsulated by the polymerization or coagulation of a suitable material to form a wall around the individual droplets.

In one application, the microcapsules which are formed can be coated on the back side of a sheet of paper or other material to form a coated back sheet. A second sheet of paper is then coated on the front side with color developing substance, typically a proton donating component such an acidic clay or phenolic resin. The microcapsule outer walls isolate the dye from the developer until the microcapsules are ruptured by the application of localized pressure. When pressure is applied by a stylus, pen, typewriter, printer or similar instrument, the microcapsules burst and the oil solution containing the solubilized dye is released and is transferred to the second sheet of paper where the dye reacts with the acid component to form an image. Carbonless paper systems of this type are described in U.S. Pat. Nos. 3,418,656 and 3,418,250, which are incorporated by reference herein in their entirety.

Solvents which are utilized in carbonless paper systems must typically be substantially colorless, have a low vapor pressure, be substantially odorless, exhibit acceptable solvency, have a suitably low freezing point, and be characterized by a low viscosity. Various types of solvents can be used in such systems and their suitability will be dependent upon the characteristics of the particular dyes and developers utilized. For example, a low viscosity solvent is generally required when phenolic acid developers are utilized in order to achieve rapid image development. By contrast, when using an acid clay developer, a higher viscosity solvent can be used with acceptable results.

Many suitable carbonless paper solvents are known. For example, certain alkyl naphthalenes are disclosed as suitable carbonless paper solvents in U.S. Pat. Nos. 3,806,463 and 4,003,589 to Konishi et al. The specific solvents are represented by the general formula:
wherein Ar is a naphthalene nucleus, R represents a $C_1$-$C_4$ alkyl group, n is an integer of 1–4, and R may be the same or different when n is 2–4, with the proviso that the total number of carbon atoms in R must be 4–6. Examples of suitable solvents listed in that patent include butylnaphthalene, dimethylpropylnaphthalene, methylbutylnaphthalene, ethylpropylnaphthalene, methylpropylnaphthalene, diethylnaphthalene, dimethylbutylnaphthalene, dimethylethylnaphthalene, dipropylnaphthalene, and trimethylpropylnaphthalene. Konishi et specifically teach that when the total number of carbon atoms in the substituted alkyl groups exceeds 6, the odor will be less observable but problems in microcapsulation and unsatisfactory dye solubility will result.

In an article published in the *Bulletin of Aichi Environmental Research Center*, No. 4, pages 114–117 (1976), Kodama reported the results of the compositional analysis of a commercial carbonless paper solvent containing alkyl naphthalenes. Among the compounds specifically identified as being present in the commercial solvent were propylnaphthalene, methylpropylnaphthalene, dimethylpropylnaphthalene, dipropylnaphthalene, methyldipropylnaphthalene, dipropylisopropenylnaphthalene, and tripropylnaphthalene. Kodama did not disclose whether the propyl moieties were n-propyl or isopropyl. Many of the alkyl naphthalenes, including methyldipropylnaphthalene, were present only in minor proportions in relation to the overall mass of the solvent mixture which was analyzed.

The use of diisopropylmethylnaphthalene as one component of a rubber processing oil having good light discoloration resistance was reported in *Chem. Ab.* 86(6): 30825r.

SUMMARY OF THE INVENTION

It is an object of this invention to provide a carbonless paper solvent that is virtually odorless but has an acceptable viscosity and is readily microencapsulated with a chromogenic material to form carbonless paper microcapsules.

It is also an object of this invention to provide a new carbonless paper solvent having acceptable odor and viscosity characteristics but which also possesses suitable dye solubilizing properties so that a uniformly mixed oil is formed within the microcapsules.

It is another object of this invention to provide a method for preparing a carbonless paper solvent from inexpensive starting materials so that a lower cost solvent can be provided.

It is a further object of this invention to provide a method for preparing a carbonless paper solvent by contacting the reactants in relative amounts which will maximize the yield of the desired solvent product.

It is a still further object of this invention to provide pressure sensitive recording or marking material which utilizes the described solvent so that desirable color developing properties are achieved.

It is a yet further object of this invention to provide carbonless paper microcapsules containing the described solvent and a chromogenic compound, which microcapsules can be used with a color developing substance to provide a pressure sensitive recording material that produces clear and dense images.

To accomplish these and other related objects of the invention, a carbonless paper solvent is provided comprising diisopropylmethylnaphthalene in an amount of between 20 and 100% of the total weight of the solvent. The solvent may also comprise diisopropylmethylnaphthalene and triisopropylmethylnaphthalene.

In another aspect, the invention comprises microcapsules comprising a dye and a carbonless paper solvent comprising diisopropylmethylnaphthalene in an amount of between 20 and 100% of the total weight of the solvent.

In yet another aspect, the invention comprises a pressure sensitive recording sheet comprising a support for carrying written or printed indicia and having coated thereon a layer of microcapsules containing a chromogenic substance and a solvent for said chromogenic substance, the solvent comprising diisopropylmethylnaphthalene in an amount of between 20 and 100% of the total weight of the solvent.

In a further aspect, the invention comprises a solvent prepared by alkylating a by-product fraction comprising methylnaphthalene and other components within a boiling point range of 200° to 400° C. with propylene under conditions sufficient to prepare diisopropylmethylnaphthalene. The other components in the by-product fraction may comprises naphthalene, biphenyl, dimethylnaphthalene, trimethylnaphthalene, and methylbiphenyl.

In yet a further aspect, the invention comprises contacting methylnaphthalene with between 1.4 and 2.0 mole equivalents of propylene under conditions sufficient to prepare diisopropylmethylnaphthalene in high yield.

DETAILED DESCRIPTION OF THE INVENTION

In accordance with the present invention, a carbonless paper solvent is provided comprising diisopropylmethylnaphthalene. It has been determined that diisopropylmethylnaphthalene is virtually odorless but has a viscosity and other properties that make it a highly desirable carbonless paper solvent. Notably, the solvent has desirable dye solubility properties which were unexpected in view of the teachings of the prior art, specifically U.S. Pat. Nos. 3,806,463 and 4,003,589 to Konishi et al. Included within the invention are individual positional isomers of diisopropylmethylnaphthalene and mixtures thereof, including those isomers having 1-methyl and 2-methyl substitutions.

In addition to diisopropylmethylnaphthalene, the solvent may include isopropylmethylnaphthalene and triisopropylmethylnaphthalene. A suitable solvent composition comprises, by weight of the total solvent composition, approximately 50 to 100% diisopropylmethylnaphthalene, 0 to 10% isopropylmethylnaphthalene, and 0 to 50% triisopropylmethylnaphthalene. A preferred composition comprises approximately 75 to 95% diisopropylmethylnaphthalene, 0 to 1% isopropylmethylnaphthalene, and 5 to 25% triisopropylmethylnaphthalene. A more preferred composition comprises 75 to 90% diisopropylmetnylnaphthalene, less than 0.5% isopropylmethylnaphthalene, and 10 to 25% triisopropylmethylnaphthalene.

The solvent composition comprising diisopropylmethylnaphthalene and optionally isopropylmethylnaphthalene and triisopropylmethylnaphthalene is used to solubilize a suitable dye in a process for making carbonless paper microcapsules. Any of various well known methods can be used for the encapsulation of the solvent and dye mixture in the microcapsules. Examples of such processes are disclosed in U.S. Pat. Nos. 3,016,308; 3,429,827; 3,578,605; and 3,712,507; 3,806,463; 4,003,589; and 4,680,056, each of which is incorporated herein by reference in its entirety.

The chromogenic material useful in conjunction with the solvent of the present invention in the formation of carbonless paper microcapsules is also known as chromogenic dye-precursor material and can include any of various suitable dyes, particularly leuco dyes which produce color under acidic conditions. Such dyes are generally from the chemical class nitroso, disazo and polyazo. Fluoran compounds of the type disclosed in U.S. Pat. No. 3,920,510 are also useful as carbonless paper dyes. Examples of suitable dyes which are commercially available include Methyl Violet, Crystal Violet, Malachite green Rhodamine B, Michler's hydrol derivatives, One-Dye-Black 1, One-Dye-Black 2, Pergascript ® dyes, and fluorane derivatives. The dye may include combinations of dyes and is generally used in a concentration of 0.1–15 parts, preferably 1–8 parts, and most preferably 4–6 parts per 100 parts by weight diisopropylmethylnaphthalene.

The acidic components used to develop the color of the dyes can be bentonite, zinc oxide, kaoline, clay, active clay, acid clay, zeolite, talc, colloidal silica, phenol-aldehyde resin, maleic acid-rosin resin, bis-phenol A, bis-phenol S, and the like. The acidic component is typically coated on a top surface of a sheet which underlies a first sheet having a bottom surface coated with microcapsules of the type described above. The acidic component can be coated on the sheet in a manner well known to those of skill in the art. It will be appreciated that other types of pressure sensitive recording material may be prepared using the microcapsules of the present invention.

Diisopropylmethylnaphthalene can be made via alkylation of methylnaphthalene (MN) with propylene using acidic catalysts such as $AlCl_3$, $AlBr_3$, hydrocarbon complexes of these Lewis acids ($HAl_2Cl_7$ complexed with cumene or toluene, for example) or other Lewis acids. Solid acid catalysts such as acidic clay, zeolites, pillared clays, and acidic resins and polymers can also be used. A preferred catalyst is the hydrocarbon soluble catalyst prepared by suspending $AlCl_3$ in toluene or cumene and adding HCl or a HCl source to form the complex.

In a presently preferred method of synthesis, the methylnaphthalene is heated to the reaction temperature, the catalyst is added, and the propylene is fed into the reaction until the desired amount of propylene is absorbed. The catalyst can also be added before the methylnaphthalene is heated to the reaction temperature.

The temperature range for the reaction is from 25° to 150° C.; the preferred range is from 80° to 130° C., and the most preferred temperature is 95° to 105° C. Higher temperatures cause increased by-product and tar formation, and propylene is absorbed slower at lower temperatures. Temperatures from 105°–130° C. can be used with only a slight increase in tar formation. The higher cost due to yield loss can be made up by a concomitant decrease in cycle time, reducing processing cost.

Pressures can be from 0 to 150 psig. In normal operation in glassware the preferred pressure would be 0 psig and propylene gas would be sparged into the reaction mixture and unreacted propylene would be vented off. In industrial operations a mixture of propylene and propane could be used to lower costs. The reaction would be run under pressure to allow all of the propylene to react and the inert propane would be vented off. Preferred pressures in such cases or with pure propylene would be 0 to 100 psig.

Preferred catalyst amounts are from 0.1 to 10 wt % $AlCl_3$; the most preferred amount for economical and chemical reasons is 1 wt % $AlCl_3$. It has also been determined that a period of transalkylation accompanied by a second catalyst dose of 1 wt % $AlCl_3$ is desirable to achieve maximum diisopropylmethylnaphthalene production. Transalkylation times of from 1 minute to 4 hours can be used; times of 30 minutes to 1.5 hours are preferred for ease of industrial operation. However, if economic reasons exist for modifying the procedure (for instance, if isopropylmethylnaphthalene and/or triisopropylmethylnaphthalene became valuable for use in some other product), the synthesis could be conducted without the transalkylation and second catalyst dose and diisopropylmethylnaphthalene would still be produced in substantial quantities.

The amount of propylene used is important in maximizing the amount of diisopropylmethylnaphthalene produced. Preferred amounts of propylene are from 1.4 to 2.0 mole equivalents. More preferred are amounts between 1.6 and 1.9 mole equivalents. It has been determined that 1.8 mole equivalents of propylene, based on the number of moles of methylnaphthalene fed to the reaction, maximizes the diisopropylmethylnaphthalene after the transalkylation period and is most preferred. More propylene produces a great deal of triisopropylmethylnaphthalene and less propylene does not produce enough diisopropylmethylnaphthalene. However, as before, if economic conditions justify more or less propylene in order to produce isopropylmethylnaphthalene or triisopropylmethylnaphthalene, substantial amounts of diisopropylmethylnaphthalene can still be made under the less preferred conditions.

The propylene can be added as fast as it can be absorbed or as fast as the reactor cooling system will allow, whichever is limiting. Typical addition times are 1 to 3 hours on the lab scale and 10 to 20 hours on the industrial scale.

A second preferred catalyst system is a solid acid catalyst such as acid clay, silica/alumina, mordenite, or zeolite. Most preferred is an acid clay such as sold under the trademark Englehard 13LM. Preferred amounts of catalyst are from 0.5 to 10 wt. % based on methylnaphthalene fed. More preferred are 1 to 7 wt. % and most preferred is 4 to 5 wt. %.

Temperatures for the solid acid catalyst systems range from 100° to 250° C., with 150° to 200° C. being preferred for the 13LM brand clay.

Because of the conditions, reactions done using solid acid catalysts are usually done in pressure vessels. Pressures of 50 to 150 psig are preferred with 75 to 125 psig most preferred.

It has been found that a period of transalkylation is helpful with the 13LM catalyst in order to optimize diisopropylmethylnaphthalene production. Such transalkylation can be carried out by heating the reaction mixture to higher temperatures after the propylene has been added. A transalkylation temperature of 200° to 300° C. is preferred, with 240° to 260° C. most preferred.

The amount of propylene used in the solid acid catalyst system is comparable to that used in the AlCl3 system. Preferred are 1.4 to 2.0 mole equivalents. Most preferred is 1.8 mole equivalents of propylene.

A third preferred catalyst system uses a Brönsted acid such as $H_2SO_4$, $CCl_3CO_2H$, $CH_3C_6H_4SO_3H$, $CH_3SO_3H$, $CF_3SO_3H$, or polymer supported acid such as Amberlyst® 15 or Nafion® H. Most preferred is $CF_3SO_3H$, at 0.1 to 5 wt. %, based on methylnaphthalene, with 0.5 to 1.5 wt. % most preferred. Preferred temperatures are 80° to 150° C., more preferred are 90° to 110° C., with 95° to 105° C. being most preferred.

Propylene amounts and system pressures preferred are similar to the previously discussed catalyst systems.

The diisopropylmethylnaphthalene prepared in this manner contains a number of positional isomers. It has been determined that diisopropylmethylnaphthalene prepared from pure 1-methylnaphthalene or from pure 2-methylnaphthalene has essentially the same physical properties and can perform the same in the microcapsules as diisopropylmethylnaphthalene prepared from a mixture of 1-methylnaphthalene and 2-methylnaphthalene. The isomeric content of the diisopropylmethylnaphthalene prepared from 1-methylnaphthalene is different than the isomeric content of the diisopropylmethylnaphthalene prepared from 2-methylnaphthalene (although small amounts of the isomers derived from the other methylnaphthalene isomer are always present). Diisopropylmethylnaphthalene prepared from a mixture of both contains more equal amounts of all isomers, although some isomers are present in larger quantities than others. Therefore, depending on the economical situation and the demand for the individual isomers in other applications, diisopropylmethylnaphthalene could be manufactured from 1-methylnaphthalene, 2-methylnaphthalene, or a mixture of both in any proportion and the product performance would be the same.

In a process in accordance with present invention, the methylnaphthalene can be isolated from an inexpensive refinery system such as gasoline end point splitter bottoms (GEPSB) or light cycle oil (LCO). Other components of these streams include naphthalene, biphenyl, dimethylnaphthalenes, trimethylnaphthalenes, and methylbiphenyls. Normally, these streams are used as fuels, so that they represent extremely inexpensive sources of methylnaphthalene.

It is not necessary to isolate the methylnaphthalene from these inexpensive refinery streams in order to make the diisopropylmethylnaphthalene. Instead, the entire by-product fraction, preferably a fraction containing components within the boiling point range of 200° to 400° C. at atmospheric pressure, and most preferably within the range of 210° to 388° C. can be alkylated and the components representing diisopropylmethylnaphthalene and optionally including isopropylmethylnaphthalene and triisopropylmethylnaphthalene can then can be isolated. The fraction which is alkylated generally includes methylnaphthalene, naphthalene, biphenyl, dimethylnaphthalene, trimethylnaphthalene and methylbiphenyl as well as other components. The diisopropylmethylnaphthalene prepared in this manner has essentially the same properties as the diisopropylmethylnaphthalene prepared from purified methylnaphthalene, 1-methylnaphthalene, or 2-methylnaphthalene. However, the cost of the excess propylene which must be used in order to prepare high yields of the diisopropylmethylnaphthalene cluster makes this synthetic route more expensive overall. The preferred method is therefore to use concentrated methylnaphthalene, 2-methylnaphthalene, or 1-methylnaphthalene as the feedstock to the diisopropylmethylnaphthalene preparation.

Distillation of the diisopropylmethylnaphthalene alkylate produces fractions containing methylnaphthalene, isopropylmethylnaphthalene, diisopropylmethylnaphthalene, and triisopropylmethylnaphthalene along with minor components such as tetralins and alkylated tetralins. The actual product used in microcapsules would be mainly diisopropylmethylnaphthalene but fractions containing isopropylmethylnaphthalene and/or triisopropylmethylnaphthalene could be used in the product to modify the characteristics of the product and improve the economics of the product. Generally, it is desirable to use as much of the distillate for product as possible in order to maximize the overall yield. Adding the more viscous and heavier triisopropylmethylnaphthalene would raise the viscosity and lower the odor of the mixture; adding the less viscous and lighter isopropylmethylnaphthalene would lower the viscosity and increase the odor. A specific formulation which is presently preferred comprises 78% diisopropylmethylnaphthalene, 0.3% isopropylmethylnaphthalene, and 15.7% triisopropylmethylnaphthalene, based on the total weight of the solvent.

The remaining alkylated fractions containing mainly methylnaphthalene, isopropylmethylnaphthalene, and triisopropylmethylnaphthalene can be combined and recycled to a subsequent alkylation after adding fresh methylnaphthalene, or the recycle blend can be alkylated directly without adding additional methylnaphthalene. In either case, the propylene amounts can be adjusted so as to provide 1.8 eq. propylene or isopropyl groups. Diisopropylmethylnaphthalene made in such a way performs the same as diisopropylmethylnaphthalene made from virgin methylnaphthalene.

The solvent comprising diisopropylmethylnaphthalene is a primary solvent. Other or secondary carbonless paper solvents can be used in the microcapsulation formulation as diluents in order to lower the overall cost of the microcapsules and/or to adjust the viscosity of the oil. These secondary solvents include kerosine, deodorized kerosine, linear alkanes, isoparaffins, alkylbenzenes, mineral oils, diaryl methanes, and other alkyl derivatives thereof. In addition, other diluents, notably those alkyl substituted naphthalenes containing a total of 6 to 10 carbon atoms in the alkyl substitutions, can be used as a diluent. Suitable examples of such alkyl naphthalenes include diisopropylnaphthalene, sec-butyldimethylnaphthalene, diethyldimethylnaphthalene, triethylnaphthalene, and triisopropylnaphthalene. In formulating the microcapsules containing diisopropylmethylnaphthalene, the diluents can be used in the amounts of 0 to 100 parts per 100 parts of the primary solvent comprising diisopropylmethylnaphthalene, preferably 20 to 80 parts per 100 parts of the primary solvent.

The following examples further exemplify the present invention and are to be read as illustrative and not in a limiting sense.

EXAMPLES 1, 2, and 3

A mixture of 2000 g of methylnaphthalene (approx. 55:45::2-MN:1-MN) and a catalyst made from 37 g AlCl$_3$, 55 g cumene, and HCl gas was heated to 100° C. and 700 g propylene was sparged into the reaction over 5.6 hr. The reaction was held at 100° C. for 1 hr then it was cooled to 60° C. The reaction was quenched with 400 mL 14.4% NaOH. After refluxing 1 hr, the layers were separated and the organic layer was washed with 400 mL water, again at reflux. The organic layer was distilled at 100 mm Hg using a 35 stage column packed with Heli-Pak B at a 5:1 reflux ratio. Fractions containing diisopropylmethylnaphthalene were combined to provide a diisopropylmethylnaphthalene blend of greater than 95% purity. Similarly prepared were diisopropyl-1-methylnaphthalene and diisopropyl-2methylnaphthalene (from purified 1-methylnaphthalene and 2-methylnaphthalene, respectively). The properties of these blends are set forth below in Table 1. From the data in the table, it can be seen that the physical properties of the diisopropylmethylnaphthalene prepared from the different sources are quite similar. The Mixed Aniline Point (MAP) and Kauri-Butanol (KB) numbers are indications of the solubilizing power of the material. The physical properties for a commercial carbonless paper solvent sold under the trademark KMC®-113 are included in the table to emphasize that though the viscosity of the diisopropylmethylnaphthalene is higher than KMC®-113, the solubilizing properties are very similar. Therefore dyes should be similarly soluble in all of the solvents in the table.

TABLE 1

| Blend | Kinematic Viscosity cSt at 100° F. | Specific Gravity (60° F./ 60° F.) | Refractive Index 25° C. | Mixed Aniline Point °C. | Kauri Butanol No. |
|---|---|---|---|---|---|
| 95% DIPMN | 10.94 | 0.9545 | 1.5675 | 18.1 | 78.9 |
| DIP-1-MN | 11.17 | 0.9559 | 1.5688 | 18.3 | 79.0 |
| DIP-2-MN | 11.42 | 0.9552 | 1.5685 | 18.1 | 76.2 |
| KMC-113 | 7.00 | 0.9574 | 1.5637 | 16.6 | 78.8 |

EXAMPLES 4, 5, 6, and 7

A study was undertaken to determine how many mole equivalents of propylene was needed to produce the maximum amount of diisopropylmethylnaphthalene. One mole of methylnaphthalene (90% purity) was alkylated with 1.4, 1.6, 1.8, and 2.0 mole eq. of propylene (based on total weight of MN feed) at 100° C. using 1 wt. % AlCl$_3$ as its toluene and HCl complex. Samples were taken after the entire amount of propylene was fed (S-1). A second 1 wt. % AlCl$_3$ dose as the catalyst complex was added and transalkylation was allowed to proceed for 1 hr at the same temperature. A second sample was then taken (S-2). GC analyses of the samples provided information as to the amounts of methylnaphthalene, diisopropylmethylnaphthalene, and triisopropylmethylnaphthalene which were present at each time and these are tabulated in Table 2.

TABLE 2

| Mole Eq. Propylene | Sample | GC % MN | GC % IPMN | GC % DIPMN | GC % TIPMN | GC % Heavies |
|---|---|---|---|---|---|---|
| 1.4 | S-1 | 13.69 | 29.90 | 30.13 | 16.69 | 1.36 |
| 1.4 | S-2 | 8.96 | 30.95 | 39.58 | 8.11 | 0.42 |
| 1.6 | S-1 | 7.72 | 25.06 | 33.53 | 22.94 | 3.67 |
| 1.6 | S-2 | 4.60 | 23.94 | 43.37 | 17.96 | 0.82 |
| 1.8 | S-1 | 4.83 | 20.59 | 36.72 | 27.95 | 4.36 |
| 1.8 | S-2 | 2.07 | 16.68 | 47.07 | 23.31 | 1.20 |
| 2.0 | S-1 | 1.64 | 9.68 | 34.38 | 32.82 | 9.87 |
| 2.0 | S-2 | 0.74 | 7.54 | 50.43 | 24.56 | 2.63 |

In each case the diisopropylmethylnaphthalene was maximized after the second transalkylation catalyst dose. In the case of 2.0 eq. propylene, considerable triisopropylmethylnaphthalene and heavies were produced. Although this triisopropylmethylnaphthalene can be recycled to a subsequent alkylation, it is difficult to obtain because of its high boiling point, and in industrial processes it is desirable to obtain as much product as possible in the first pass through the system. In the cases of the 1.4 and 1.6 eq. propylene reactions, insufficient diisopropylmethylnaphthalene was produced. Therefore, the 1.8 eq. propylene case is optimum. In actual practice, 1.7 to 1.9 eq. can be used with little difference in yield.

EXAMPLES 8, 9, 10 and 11

Methylnaphthalene was heated with 5 wt. % 13LM clay to 130°-140° C. and 1.8 eq. propylene was added (40-60 psig) and sample S-1 was taken. The mixture was heated to 250° C. for 1 hr. and sample s-2 was taken. The results are shown in Table 3.

Methylnaphthalene was heated with 5 wt. % SAB-10 (UOP Silica/Alumina, 63% Alumina, 1/16" pellets) to 250° C. and 1.7 eq. propylene was added (60-100 psig). Results are tabulated below.

Methylnaphthalene was heated with 5 wt. % M-8(48) (UOP Modenite, calcined at 500° C. 8 hrs.) at 275° C. and 1.5 eq. propylene was added (40-100 psig). The reaction was slow to take up propylene. Results are tabulated below.

Methylnaphthalene was heated with 1 wt. % $CF_3SO_3H$ and 1.8 eq. propylene was sparged into the mixture. Results are tabulated below.

TABLE 3

| Catalyst | Sample | GC % MN | GC % IPMN | GC % DIPMN | GC % TIPMN | GC % Heavies |
|---|---|---|---|---|---|---|
| 13LM | S-1 | 6.78 | 21.43 | 33.57 | 28.09 | 8.33 |
|  | S-2 | 1.84 | 19.19 | 53.45 | 15.80 | 5.01 |
| SAB 10 | Final | 4.62 | 23.57 | 46.44 | 20.31 | 2.54 |
| M-8(48) | Final | 7.21 | 41.84 | 36.49 | 2.80 | 1.72 |
| $CF_3SO_3H$ | Final | 5.55 | 20.51 | 39.03 | 28.60 | 4.46 |

EXAMPLE 12

To 100 parts diisopropylmethylnaphthalene is added 8 parts leuco black dye of the alkylamino-fluorane type. The mixture is warmed to 100° F. and agitated to give complete solution. To the resultant solution is added 100 parts of mixed triisopropyltoluene isomers (TIPT) and the entire solution allowed to equilibrate. This solution, added to 150 parts aqueous solution containing 35 parts gum arabic, gives on agitation a stable suspension which, upon addition of 200 parts of a 12% gelatine solution, sufficient sodium hydroxide to maintain the pH at 9 and additional water (800 parts) gives a suspension which, upon further addition of acetic acid to pH=4 to 4.5 under agitation yields a suspension of oil microdroplets. Further addition of formaldehyde solution (4 parts $CH_2O$) and subsequent adjustment of pH to 9.65 causes hardening of the microdroplets to capsules. These microcapsules when applied by standard techniques to paper at a rate of about 5 gm/m$^2$, and dried, produced paper ready for acid development by clays or by acid resins, when broken by pressure from a stylus.

Having thus described the invention, what is claimed is:

1. A recording sheet comprising a support for carrying written or printed indicia having coated thereon a continuous layer of microcapsules containing a chromegnic substance and a solvent for said substance, said solvent comprising 75% to 95% by weight diisopropylmethylnaphthalene and 5% to 25% by weight triisopropylmethylnaphthalene.

2. The recording sheet as set forth in claim 1, comprising approximately 78% by weight diisopropylmethylnaphthalene and approximately 15.7% by weight triisopropylmethylnaphthalene.

* * * * *